United States Patent [19]

Berthold et al.

[11] Patent Number: 5,216,483
[45] Date of Patent: Jun. 1, 1993

[54] FLUORESCENCE ANALYZER FOR LIGNIN

[75] Inventors: John W. Berthold, Salem; Michael L. Malito, Hubbard; Larry Jeffers, Alliance, all of Ohio

[73] Assignee: The Babcock & Wilcox Company, New Orleans, La.

[21] Appl. No.: 763,712

[22] Filed: Sep. 23, 1991

[51] Int. Cl.$^5$ .......................... G01J 3/30; G01N 21/64; D21C 7/14
[52] U.S. Cl. .................. 356/318; 250/461.1; 162/49
[58] Field of Search .................. 356/317–318, 356/417; 250/458.1, 459.1, 461.1, 461.2; 162/49, 198, 263

[56] References Cited

U.S. PATENT DOCUMENTS

| 4,650,336 | 3/1987 | Moll ..................... 356/317 |
| 4,837,446 | 6/1989 | Renard et al. .......... 250/461.1 |
| 4,842,689 | 6/1989 | Jikka et al. ............. 162/49 |
| 4,889,593 | 12/1989 | Tikka et al. ............ 162/49 |
| 4,895,618 | 1/1990 | Tikka et al. ............ 162/49 |

FOREIGN PATENT DOCUMENTS 2231958A 11/1990 United Kingdom ................ 356/317

OTHER PUBLICATIONS

Kubulnieks, E. et al., "The STFI OPTI-Kappa Analyzer, Applications and Accuracy," *Tappi Journal*, Nov. 1987 pp. 38–42.

Horvath, J. J. and Semerjian, H. G., "Laser Excited Fluorescence Studies of Black Liquor," SPIE, Quebec City, Canada, Jun. 4–6 1986 pp. 258–264.

TAPPI Procedure T-236 hm-85, "Kappa Number of Pulp" publication date unknown—admitted prior art.

Hartler, N. and Norrstrom, H., "Light Absorbing Properties of Pulp and Pulp Components," *TAPPI Journal*, vol. 52, No. 9, Sep. 1969.

Kleinert, T. N. and Joyce, C. S., "Short Wavelength Ultraviolet Absorption of Various Lignins and Related Substances", Part I, *Pulp and Paper Mag Can.* 58, No. 5, Apr. 1957, pp. 154–158.

Id., Part II, No. 6, May 1957, pp. 131–148.
Id., Part III, No. 7, Jun. 1957, pp. 215–219.
Id., Part IV, Oct. 1957, pp. 147–152.

Norrstrom, B. and Teder, A., "Absorption Bands in Electronic Spectra of Lignins, Part 2, Band Intensities for Alkeli Lignins from Spruce", *Svensk Papperstidning*, Jun. 15, 1971.

Sjostrom, E. and Haglund, P., "Spectrophotometric Determination of the Dissolution of Lignin During Sulfite Cooking," TAPPI Journal, vol. 47, No. 5, May 1964.

Baumgartner, D. J., Feldman, M. H., and Gibbons, C. L., "A Procedure for Tracing Kraft Mill Effluent from an Ocean by Constituent Fluorescence," *Water Research*, Pergamom Press, vol. 5, 1971, pp. 533–544.

Bublitz, W. J. and Wade, D. C., "Applied Waste Liquor Fluorescence to Control Pulp Quality", *Svensk Papperstidning*, No. 18, 1979.

(List continued on next page.)

*Primary Examiner*—Vincent P. McGraw
*Assistant Examiner*—K. P. Hantis
*Attorney, Agent, or Firm*—Robert J. Edwards; Vytas R. Matas; Daniel S. Kalka

[57] ABSTRACT

A method and apparatus for measuring lignin concentration in a sample of wood pulp or black liquor comprises a light emitting arrangement for emitting an excitation light through optical fiber bundles into a probe which has an undiluted sensing end facing the sample. The excitation light causes the lignin concentration to produce fluorescent emission light which is then conveyed through the probe to analyzing equipment which measures the intensity of the emission light. Measures are taken to maximize the emission light intensity which is due to lignin concentration and distinguish it from background and interfering light. The fluorescent light intensity is found to drop off in a predictable manner with increased lignin concentration.

10 Claims, 15 Drawing Sheets

OTHER PUBLICATIONS

Wilander, A., Kvarnas, H. and Lindell, T., "A Modified Fluorometric Method for Measurement of Lignin Sulfonates and its In Situ Application in Natural Waters," *Water Research,* vol. 8, pp. 1037–1045, 1974.

Denias, J. N., *Excited State Lifetime Measurements,* Academic Press, New York 1983, pp. 53–58.

Tikka, P. O. and Virkola, N. E., "A New Kraft Pulping Analyzer for Monitoring Organic and Inorganic Substances," TAPPI Journal, Jun., 1966, pp. 66–71.

Williams, D. J., "The Application of Ultra-Violet Absorption Characteristic of Lignin to the Control of Pulp Uniformity," Appita, vol. 22, No. 2, Sep. 1968, pp. 45–52.

Carpart, R., Obese-Jecty, K., LeCardinal, G., and Gelus, M. "Contribution to the On-Line Kraft Pulping Control," PRP 4 Proceedings Ghent, 1980.

Bublitz, W. J., "Fluorescence of Pulping Liquors: A Tool for Digester Control?", *TAPPI,* Jun. 1981 vol. 64, No. 6, pp. 73–76.

Copies of Overheads used in two oral presentations: (1) Optical Society of America; and (2) Department of Energy/Industry Sensor Working Group Meeting, both oral presentations Oct. 1989.

Abstract published for above presentations.

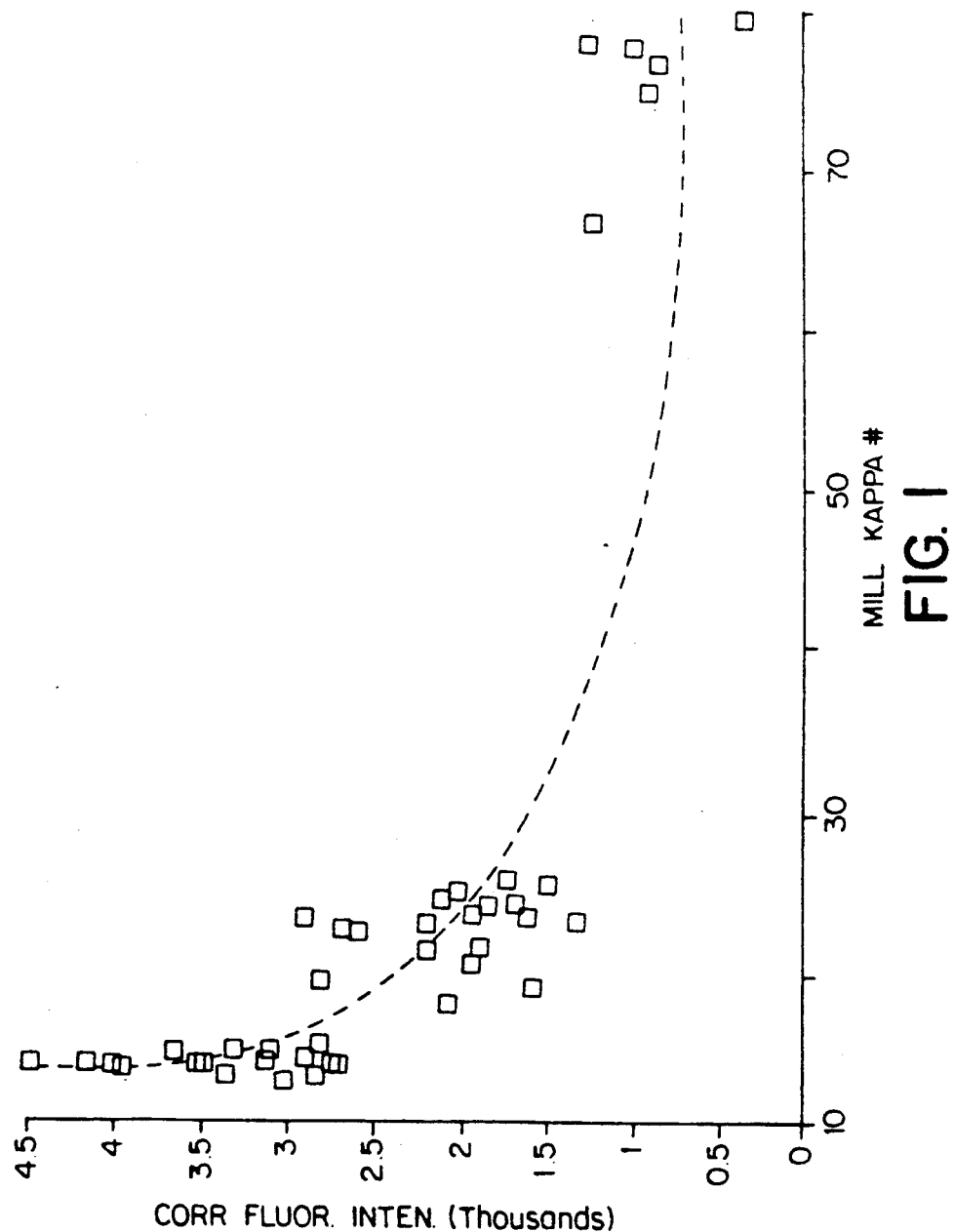

FLUORESCENCE ANALYZER FOR LIGNIN

This invention was made with Government support under Contract Number DOE: DE-FC05-90CE40905 awarded by the Department of Energy (DOE). The Government has certain rights in this invention.

FIELD AND BACKGROUND OF THE INVENTION

The present invention relates in general to the pulp and paper industry, and in particular to a new and useful analyzer for monitoring the concentration of lignin in wood pulp and black liquor.

In the pulp and paper industry, the production of paper products requires that lignin be partially removed from the wood chip feed stock prior to making paper products. Lignin is a polymer of complex chemical structure which "cements" the wood's cellulose fibers together. The process by which lignin is removed is referred to as delignification. The most prevalent method of delignification is by chemical means in which raw wood chips and chemicals are combined at a controlled pressure and temperature in a vessel known as a digester. While in the digester, the amount of lignin removed from the wood chips determines the product quality, the product yield, the amount of energy consumed, the quantity of chemicals consumed, and the product cost. Fluid drained from the digester during delignification contains lignin removed from the wood chips and is referred to as "black liquor". The black liquor is used as fuel in a boiler to produce process steam.

The measurement of the residual lignin remaining in the pulp, which exits the digester, is most commonly carried out by laboratory analysis of hourly samples of the digester output (samples are typically obtained at the last stage of the brownstock washer). The lab analysis takes approximately one hour and therefore is a poor method for providing process control feedback and cannot be used for feedforward control. This lab analysis is a back titration method which measures the consumption of the potassium permanganate and is only an approximation to the lignin concentration. The output of titration analysis is referred to as "KAPPA Number" and the procedure is documented in TAPPI procedure T236 hm-88, "KAPPA Number of Pulp[. A number of manufacturers have produced automatic sampling and titration devices which have been tried in pulp mill situations but they have been mostly unsuccessful in providing accurate long term results and do not reduce the hour delay between the process and measurement of the residual lignin.

The ultraviolet absorption and fluorescence properties of lignin have long been known and a number of researchers have reported results of measurements in solutions containing lignin. Both the absorption techniques (e.g. see Kleinert, T. N. and Joyce, C. S., "Short Wavelength Ultraviolet Absorption of Various Lignins and Related Substances," Part IV, *Pulp and Paper Mag. Can.* 58, Oct. 1957, pp. 147-152) and the fluorescence techniques (e.g. see Demas, J. N., *Excited State Lifetime Measurements*, Academic Press, New York 1983) have all been applied to very dilute solutions. The fluorescence techniques have been used primarily as a method of detecting trace quantities in effluent streams. All of these approaches made use of the very dilute lignin solutions where the absorption and fluorescence signal are linearly related to lignin concentration. The dilution is typically 2,000–10,000 times more dilute than the concentration of lignin in "black liquor" found in the pulping process and thus requires precise sample preparation prior to measurement. A number of devices which attempt to monitor the lignin concentration in "black liquor" during the pulping process by UV absorption techniques (alone or in combination with chemical analysis) have been produced. These devices require sample preparation and dilution prior to measurement and are therefore not in-situ, not real-time, and introduce sampling and dilution errors. See Tikka, P. O., and Virkola, N. E., "A New Kraft Pulping Analyzer for Monitoring Organic and Inorganic Substances", *TAPPI Journal*, June, 1966, pp. 66-71; Williams, D. J., "The Application of Ultra-Violet Absorption Characteristic of Lignin to the Control of Pulp Uniformity", *Appita*, Vol. 22, No. 2, September, 1968, pp. 45-52; and Carpart, R., Obese-Jecty, K., Le Cardinal, G. and Gelus, M., "Contribution of the On-Line Kraft Pulping Control", *PRP 4 Proceedings*, Ghent, 1980.

Use of ultraviolet absorption has recently been extended to the measurement of residual lignin in wood pulp (see Kubulnieks, E., Lundqvist, S., and Pettersson, T., "The STFI OPTI-Kappa Analyzer, Applications and Accuracy", *TAPPI Journal*, November, 1987, pp. 38-42). The device disclosed in this article is marketed by Asea Brown Boveri under the trade name "Opti-Kappa Analyzer". In this approach, the pulp stream is sampled approximately once every 5 minutes. The pulp sample is screened, washed thoroughly, and diluted significantly. The diluted sample is circulated in a loop where UV light absorption is measured over a prescribed time period and the pulp concentration in the slurry (i.e., pulp consistency) is measured independently. This system involves sampling error, screening error, and pulp consistency measurement error. Although the system provides results much faster than the conventional lab titration process, it is still off-line. The washing requirements of this device are stringent since any small amount of black liquor remaining in the diluted solution will absorb UV light and produce error. Bannier Technology Group (BTG Inc.) also offers a device which operates on similar principle but uses UV reflection rather than absorption. The BTG device is marketed under the name "KNA-5000 Kappa Number Analyzer".

All of the investigations and devices discussed so far used broad band lamps as the source of UV light. In 1986, researchers at the National Bureau of Standards (see Horvath, J. J., Semerjian, H. G., "Laser Excited Fluorescence Studies of Black Liquor," *Proceedings of The SPIE*, Vol. 665, June, 1986, pp 258-264) performed fluorescence tests on diluted black liquor samples using a laser as the source of UV light. Although their investigation resulted in better signal-to-noise ratios, they essentially did not extend the art beyond that of previous investigators. They were only able to obtain a functional relationship between fluorescence and lignin concentration in very dilute samples of black liquor (less than 1300 PPM, which is orders of magnitude less than the in-situ concentrations) and did not investigate pulp at all. They did not provide any insight into how one might be able to use either UV absorption or fluorescence techniques to extend the useful measurement range beyond the highly diluted state.

They did mention that this process was a candidate for in-situ monitoring but provided no rational explanation of how the dilution requirement could be overcome. They also mentioned that the measurement could be made more acceptable for field use by using optical fibers to guide the UV excitation light to the process stream and carry the fluorescence signal back to the opto-electronics unit.

SUMMARY OF THE INVENTION

Based on a desire to meet the need for an on-line, real-time device which could monitor the concentration of lignin in wood pulp and black liquor, the present invention resulted from a project which examined the fluorescence of black liquor and wood pulp under excitation by various narrow band wavelengths of UV light. It is believed that these wood pulp experiments were the first ever performed and the results are novel in that a completely unexpected phenomenon was discovered. Namely, when the concentration of lignin in the specimen is increased beyond the very dilute regime, which had been studied earlier by others, the fluorescence intensity levels off and then begins to decrease with increasing concentrations of lignin. The region of most interest to on-line pulping is represented by a monotonically decreasing function of fluorescence vs. lignin concentration. This monotonically decreasing function of fluorescence vs. concentration is known as the "quenched fluorescence regime". Although the quenching phenomenon in molecular substances has been known for a long time, the shape of that curve, which can be flat, erratic, or decreasing, had never been empirically determined for lignin containing substance prior to the present invention. This is important because the steep monotonically decreasing function discovered is not common and is the only curve that would make the technique of the invention valuable in measuring lignin in the undiluted product.

It has also been found that the fluorescence signal which is produced in undiluted wood pulp, as it flows past the last brownstock washer in the pulp mill, is unaffected by trace amounts of black liquor remaining in the pulp at that stage of the process. This means that the measurement can be made on-line without having to wash the pulp beyond the level already performed in the normal pulping process.

The invention also includes three technical enhancements which improve accuracy and resolution of the measurement. These three enhancements are:

A. Use of more than one UV excitation wavelength to discriminate between the fluorescence of lignin and any potential interferents.

B. Use of time resolved fluorescence to eliminate unwanted fluorescence and to make the functional relationship between fluorescence and lignin concentration even more steep, thus resulting in improved resolution in highly concentrated substances.

C. Use of phase resolved fluorescence to eliminate the unwanted fluorescence.

The invention also uses mechanical distancing, special optics, and proximity sensors to make possible the measurement of a moving pulp mat whose distance from the probe is varying. For the measurement of pulp and/or black liquor in a pipe line the invention also uses a number of probe configurations.

The invention further includes the results of investigating variable excitation wavelengths, phase resolved fluorescence, and time resolved fluorescence. All of these methods have been successful in discriminating the fluorescence of lignin in the presence of other fluorescent species in undiluted wood pulp.

Accordingly, an object of the present invention is to provide an apparatus for and a method of monitoring lignin concentrations in wood pulp and black liquor on a real-time, on-line basis.

A further object of the the invention is to provide an apparatus for monitoring lignin concentration which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiments of the invention are illustrated.

BRIEF DESCRIPTION OF THE DRAWINGS

In the drawings:

FIG. 1 is a graph plotting fluorescence vs. lignin concentration as measured by pulp KAPPA Number in pulp monitored according to the present invention using continuous excitation at 334 nm, which demonstrates the functional relationship at undiluted lignin concentrations;

DESCRIPTION OF THE PREFERRED EMBODIMENTS

Figure 1A:
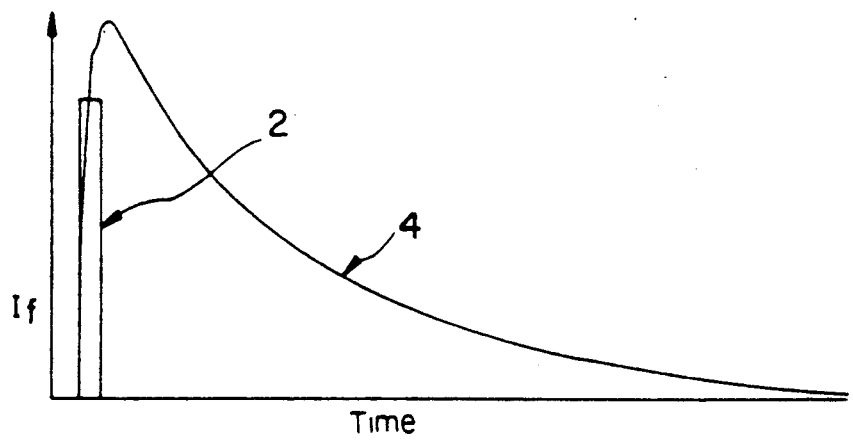
FIG. 1A is a graph plotting light intensity against time for an excitation light pulse and resulting fluorescent behavior of fluorescing material in general.

Referring to the drawings in particular, the invention embodied therein comprises a method and apparatus of monitoring lignin concentration in wood pulp or black liquor, which takes advantage of the predictable and reproducible fall off in fluorescence as lignin concentration increases, illustrated in the graph of FIG. 1. This portion of the curve is referred to as the quenched fluorescence regime. FIG. 1 shows the unwashed specimen test results (RES1) with an excitation wavelength of 334 nm.

Figure 3A:
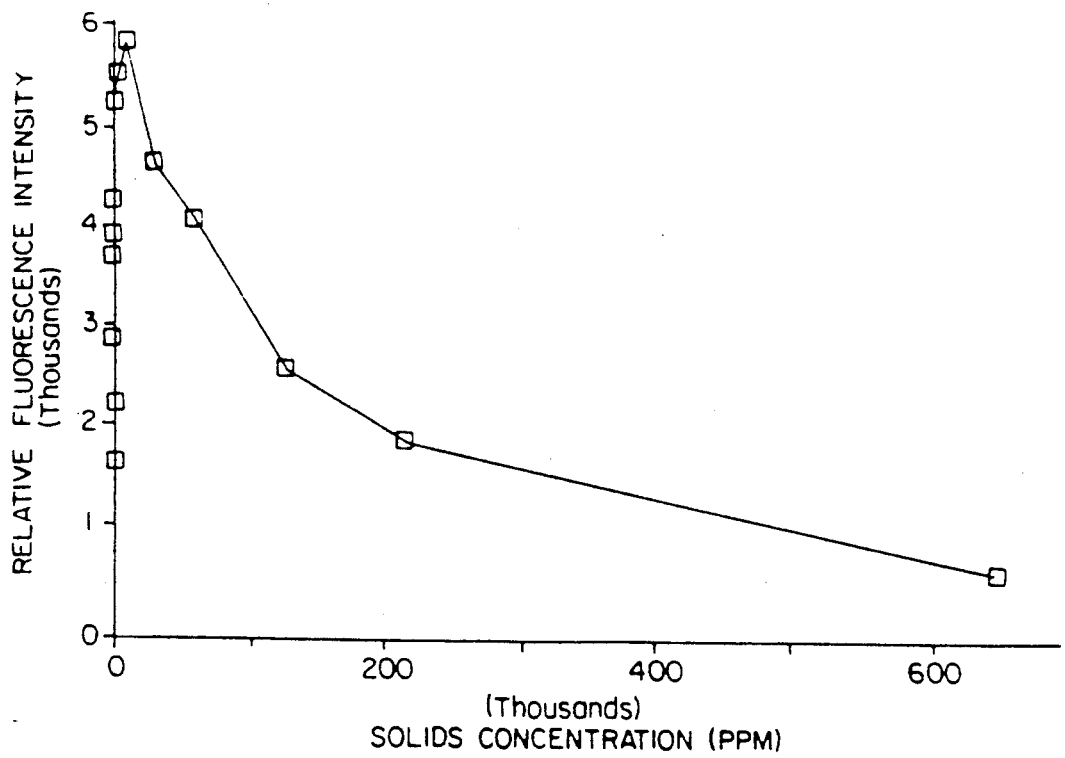
FIG. 3A is a composite graph plotting fluorescence intensity vs. lignin concentration (PPM) discovered using the lab set up of FIG. 2 on a variously diluted black liquor sample (BL5) at an excitation wavelength of 334 nm.

Referring to the graph shown in FIG. 3A, the quenched side begins immediately after the peak on the curve and continues to include everything to the right side of the curve therefrom. At an excitation wavelength of 334 nm and other nearby wavelengths, the lignin concentration expressed in KAPPA Number falls off in such a predictable manner that fluorescence intensity can be utilized to calculate lignin concentration.

Excitation wavelengths less than 500 nm can be used to excite lignin fluorescence. Shorter wavelengths are preferred since they produce stronger signals and are more selective than longer wavelengths. The actual wavelength chosen depends upon the embodiment. Results have been obtained using the 313 nm, 334 nm, and 365 nm lines (wavelengths) of a Mercury arc lamp, the 325 nm line of a HeCd laser, the 337 nm line of a pulsed $N_2$ laser, and 360–500 nm wavelengths of a pulsed dye laser.

FIG. 1A illustrates the temporal behavior of the fluorescing material when excited by a pulse of light (2) having short duration. During the excitation pulse, the fluorescence intensity (4) rapidly. After the excitation pulse, fluorescence begins an exponential decay with a characteristic and identifiable time constant.

Figure 1B:
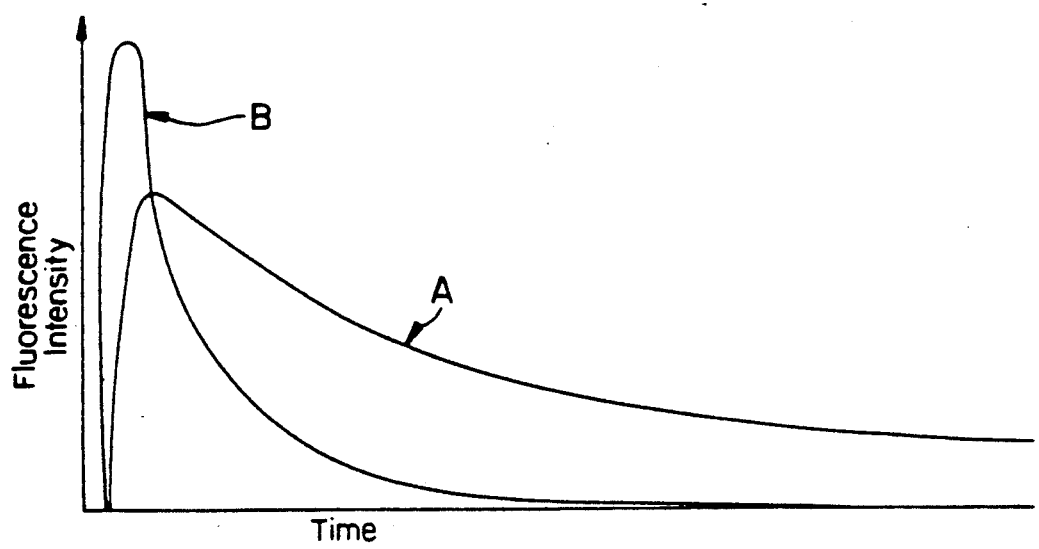
FIG. 1B is a graph plotting fluorescence intensity against time for different fluorescing species.

FIG. 1B shows the fluorescence from two different species (A,B) under pulsed excitation conditions. The decay time constant of species A is much longer than that of B. If a sample to be analyzed according to the present invention contains both species, the resultant signal will be the sum of the two curves in FIG. 1B.

In a conventional, non-time resolved approach, one would generate a signal proportional to the total area under the resultant curve. In other words, instead of looking at how the signal changes with time, one would merely integrate the total signal over the total time of fluorescence.

When the sample contains only one or the other of the components A and B, this type of signal is sufficient to provide a measure of the concentration of that component. If both components are present, one cannot separate the contributions of the two and, hence, cannot determine the concentration of either.

In time resolved fluorescence spectroscopy the invention makes use of the additional information that component B fluorescence decays much more rapidly than does that from A. If the decay time difference is large, one can simply wait to turn the detector on until virtually all of the fluorescence from B is gone. The remaining signal, although smaller than the total, can then be attributed to A and therefore used to find the concentration of A. Knowing this concentration of A, the B concentration can then be calculated from the conventional "all time" measurement.

In fact, the difference in decay times need not be so large as to allow the complete decay of B before making the measurement. As long as the time constants are known, any two measurements made over two different time intervals, provide the information necessary to calculate the concentration of both A and B.

Phase sensitive spectroscopy of the invention is based on the same effect, e.g., the differential in decay times. Instrumentally, however, it is altogether different. Instead of pulsing the excitation and making measurements at known time intervals after the pulse, as in the time resolved approach, a continuous source is used. This source is then rapidly modulated. This in turn modulates the fluorescence signal. In other words, if one turns the excitation on and off at some rate, the fluorescence signal will turn on and off at the same rate. Because of the time constant, however, the fluorescence signal does not shut off at the same time as the source but at some time later determined by the decay time constant. The fluorescence signal then has the same frequency as the source modulation but is delayed in phase, the phase delay being proportional to the decay time constant. When the sample has two or more components, the fluorescent signal is a sum of two or more signals all having the same frequency but each differing in phase. These signals can be electronically separated on the basis of this phase difference and used separately to determine the concentration of individual components.

The present invention can thus distinguish the fluorescence due to lignin even when other fluorescing materials are present in the sample, as long as the spectral characteristic of each material is known in advance.

Figure 2:
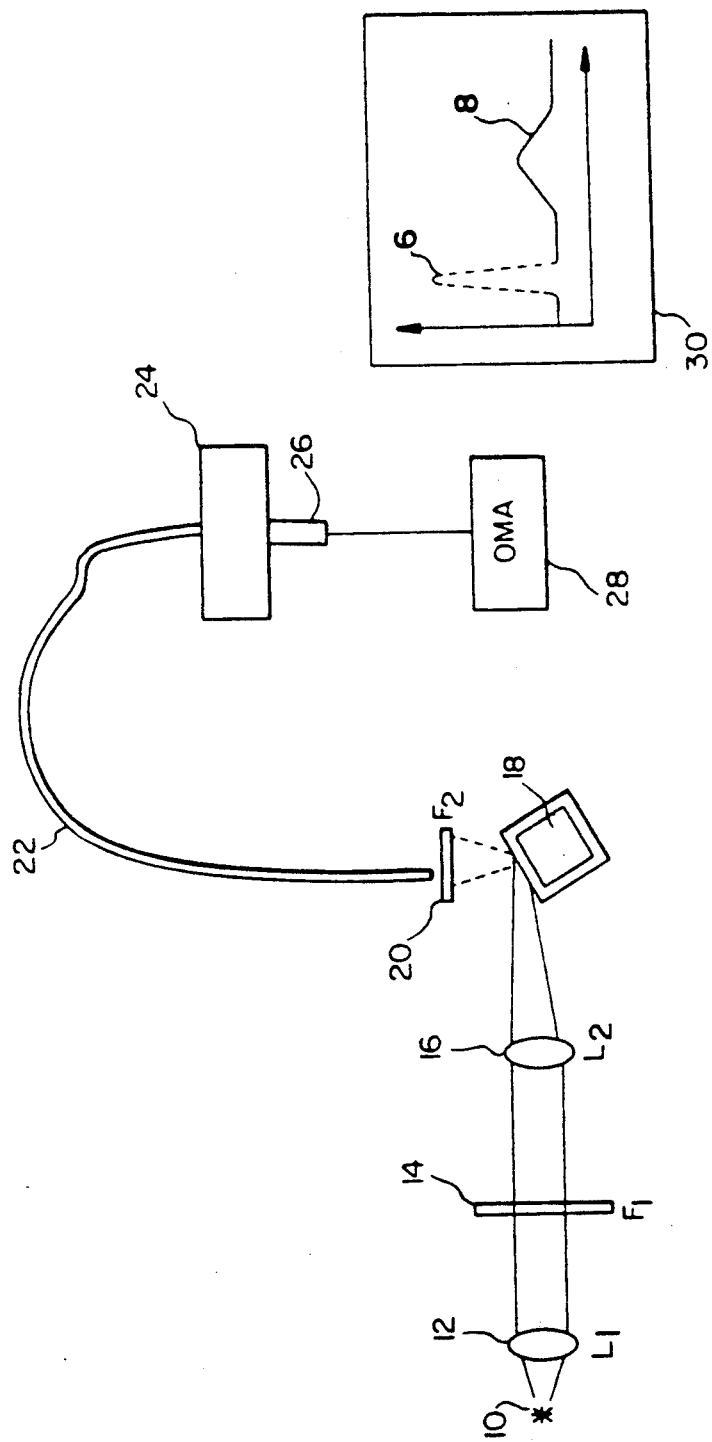
FIG. 2 is a schematic block diagram of a lab set up used in accordance with the present invention using continuous excitation.
Figure 3B:
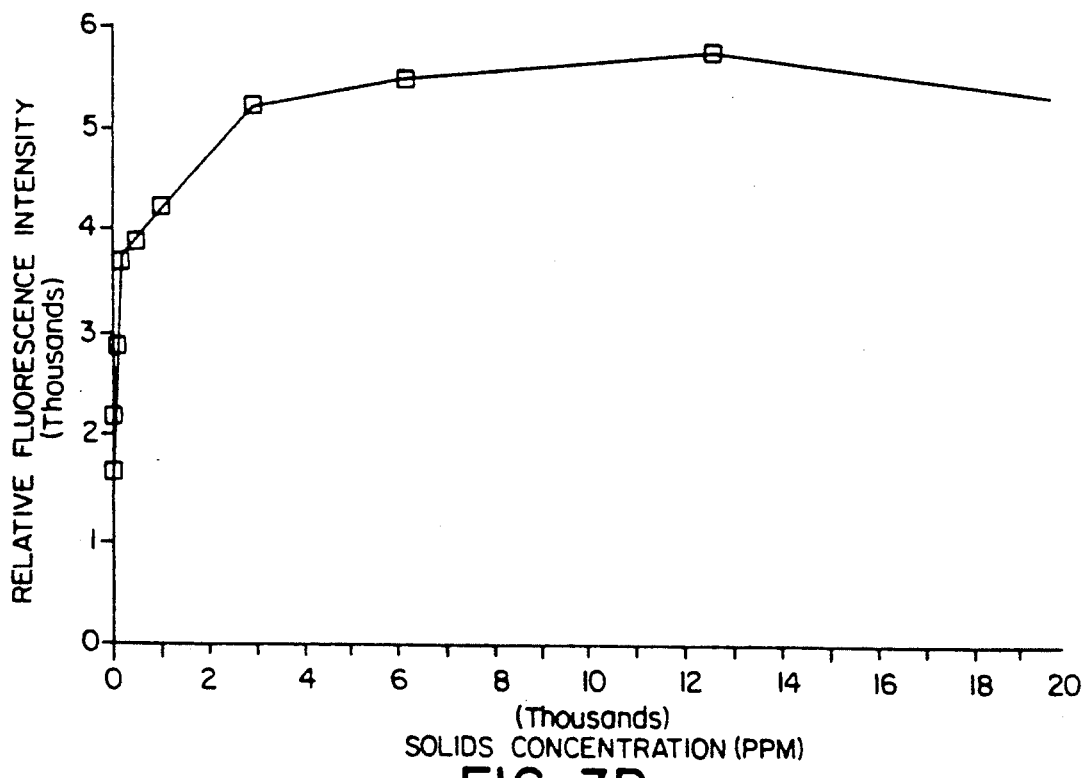
FIG. 3B is a composite graph plotting fluorescence intensity vs. lignin concentration (ppm) discovered using the lab set up of FIG. 2 on a variously diluted black liquor sample (BL3) which si the same as (BL5) with expanded axis.

FIG. 2 illustrates an apparatus of the present invention for collecting fluorescence intensity data which comprises a light source (10) in the form of a mercury arc lamp. Lamp (10) shines light through an optical system in the form of a lens (12), a first filter (14) and a second lens (16) which focuses the light onto a sample cell (18) containing pulp or black liquor. Fluorescent light emitted from sample cell (18) passes through a second filter (20) and along a fiber optic bundle (22), to a monochromator (24). A light intensity detector (26) such as "SIT" detector is connected to the output of monochromator (24) to generate a signal which is processed in circuitry (28). Circuitry (28) is connected to display means (30) which produces a graphic representation of fluorescent intensity plotted against wavelength showing an excitation peak (6) and an emission peak (8). For an excitation wavelength of 334 nm, the concentration of solids in black liquor, and thus the concentration of lignin, in sample cell (18) is changed to produce the results illustrated in FIGS. 3 A and 3B for a solids concentration approaching 0 up to a concentration of about 650,000 parts per million (ppm). The concentration of lignin in the black liquor is roughly 50% of the solids concentration. Although fluorescence increases up to about 13,000 ppm, it thereafter drops off as shown in FIG. 3A.

Figure 4:
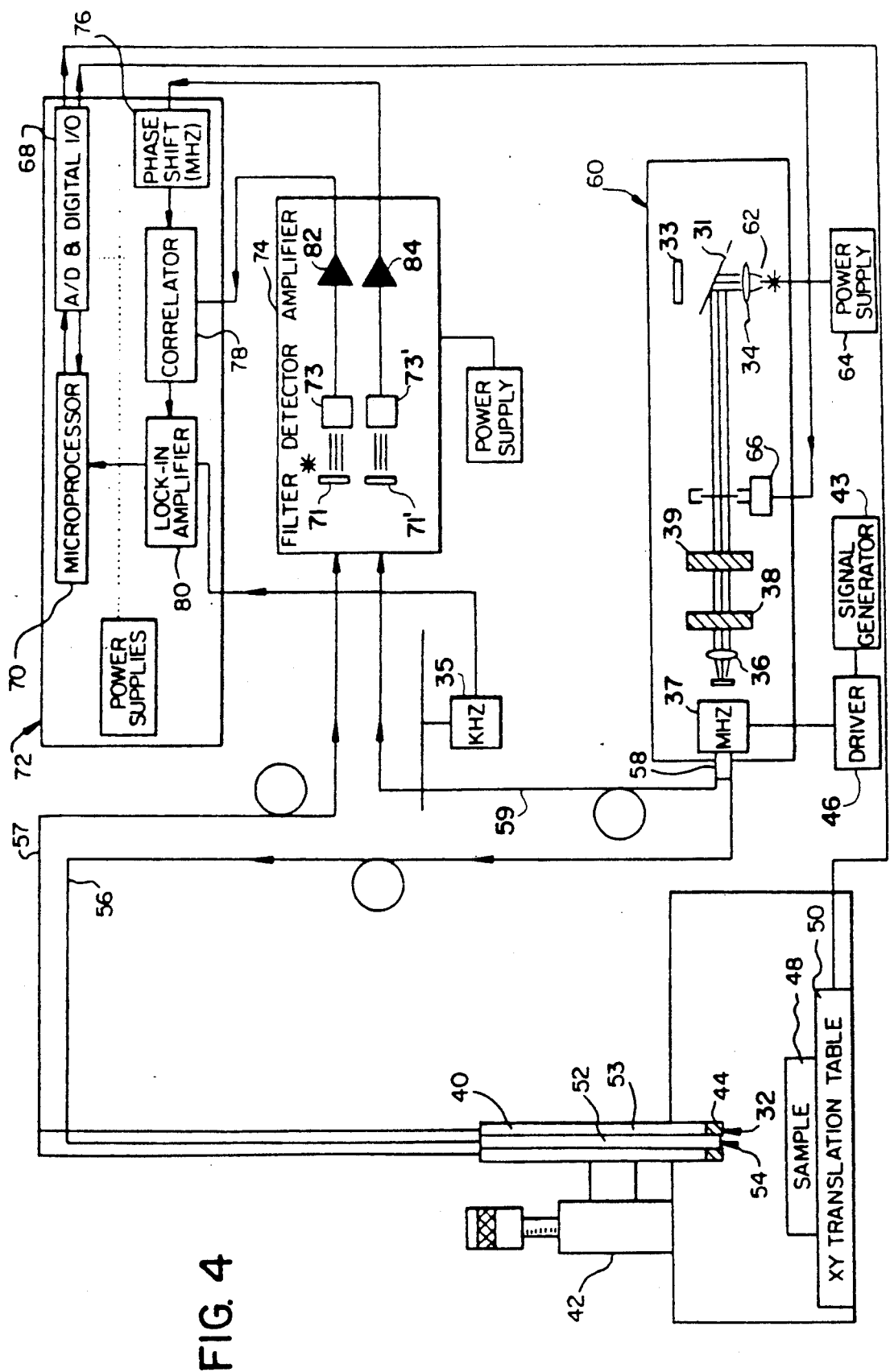
FIG. 4 is a block diagram of an apparatus used to measure lignin concentration in a black liquor sample, using phase resolved fluorescence.

FIG. 4 schematically illustrates an apparatus which can be utilized for practicing the phase resolved version of present invention off-line. For on-line operation, one of the probe configurations shown in FIGS. 9-21 may be incorporated. The apparatus comprises a probe (40) attached to depth adjusting means (42) for moving the detecting end (44) of the probe closer to or further away from a sample (48) for example a wood pulp mat, held on a precision XY translation table (50) which can change the relative position of the mat (48) to the detecting end of the probe (40). Probe (40) comprises a central excitation tube (52) having a band-pass filter (54) at its lower end for passing a selected wavelength, such as 334 nm, of excitation light. Light is supplied to the excitation tube (52) by excitation optical fibers (56) attached at a coupler (58) to an excitation source generally designated (60). Excitation source (60) has a light source (62) powered by a power supply (64) for passing light through an optical arrangement with a cold mirror (31) and heat sink (33) including an electric shutter (66) which is controlled by an input/output (I/O) device (68) connected to a microprocessor (70) in a system processor arrangement (72). Light amplitude modulator (37) modulates the light source (62) and signal generator (43) establishes the frequency of modulation. Driver (46) amplifies the output signal of the signal generator in a known manner. Other lenses and filters, for example, lenses (34), (36), vertical polarizer (38), and bandpass filter (39), are provided in excitation source (60) for conditioning the light supplied through filter (54) onto the sample (48). Fluorescent light from the sample (48) is conducted through a long pass filter (32) and a tube (53) forming another part of probe (40). This light is conducted along an optical fiber bundle (57) to an opto-electronic package (74). Coupler (58) also provides a reference light source by way of referenced fiber (59) to the opto-electronics package (74). Chopper (35) supplies the reference signal to lock-in amplifier (80). The opto-electronics means or package (74) includes the following components for both sample and reference signals: filters (71, 71'), detectors (73, 73'), and amplifiers (82, 84). The reference light is supplied to a phase shift element (76) and then compared with respect to phase, to the fluorescent light in a correlator (78).

The correlation or lack thereof between the source and fluorescent light is applied to the microprocessor (70) through a lock-in amplifier (80). Microprocessor (70) is programmed with the information necessary to calculate lignin concentration from phase shift information, the phase shift information corresponding to the fluorescent light intensity due to fluorescent lignin in the sample. The signals from microprocessor (70) can also be utilized to move the shutter (66) and the XY translation table (50) for taking a fresh reading.

Figure 5:
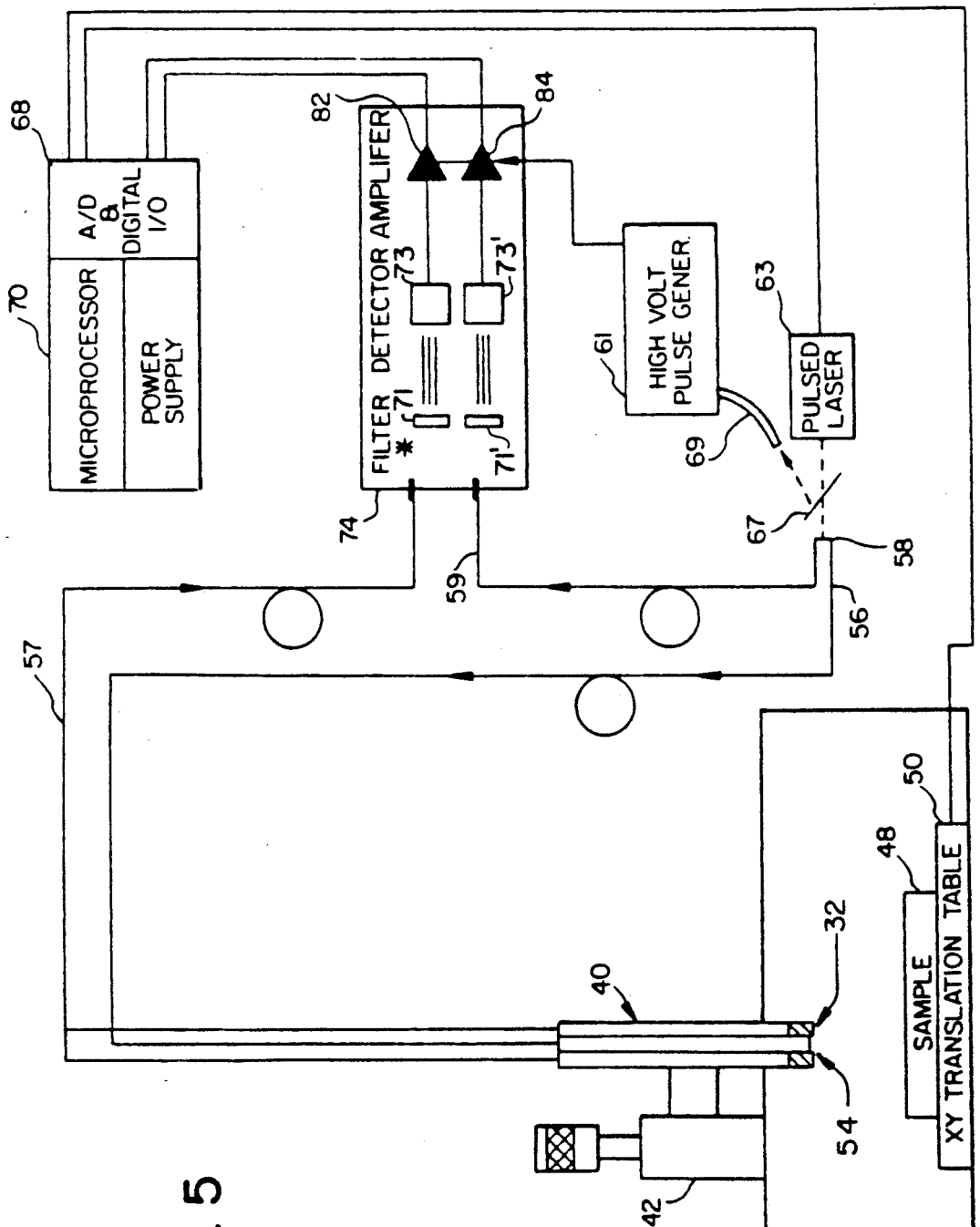
FIG. 5 is a view similar to FIG. 4 of an apparatus for measuring lignin concentration on a time resolved basis.

FIG. 5 is an embodiment similar to FIG. 4 for measuring the intensity on a time resolved basis. The same reference numerals are utilized to designate the same or functionally similar parts. Where the parts have already been described in connection with FIG. 4, the description will not be repeated.

The time resolved embodiment of FIG. 5 utilizes a pulsed laser (63) operating at a selected wavelength such as 337 nm which shines light through a beam splitter (67), to the optical fiber bundle (56) carrying the excitation light. A fiber bundle (69) conveys the divided part of the split beam from laser (63), to a high voltage pulse generator (61) which applies gating pulses to a pair of high speed detectors or detector amplifiers (82, 84) in opto-electronics package (74) which may contain a monochromator at the asterisk. The amplifiers (82, 84) respectively receive pulses proportional to light intensity on emission fibers (57), corresponding to the fluorescent intensity from the lignin in sample (48), and an optical fiber bundle (59) which supplies pulsed laser light from the coupler (58). The opto-electronics package (74) thus provides time resolved comparisons between excitation and fluorescent light of sample (48), which is processed in microprocessor (70).

Figures 6A, 6B:
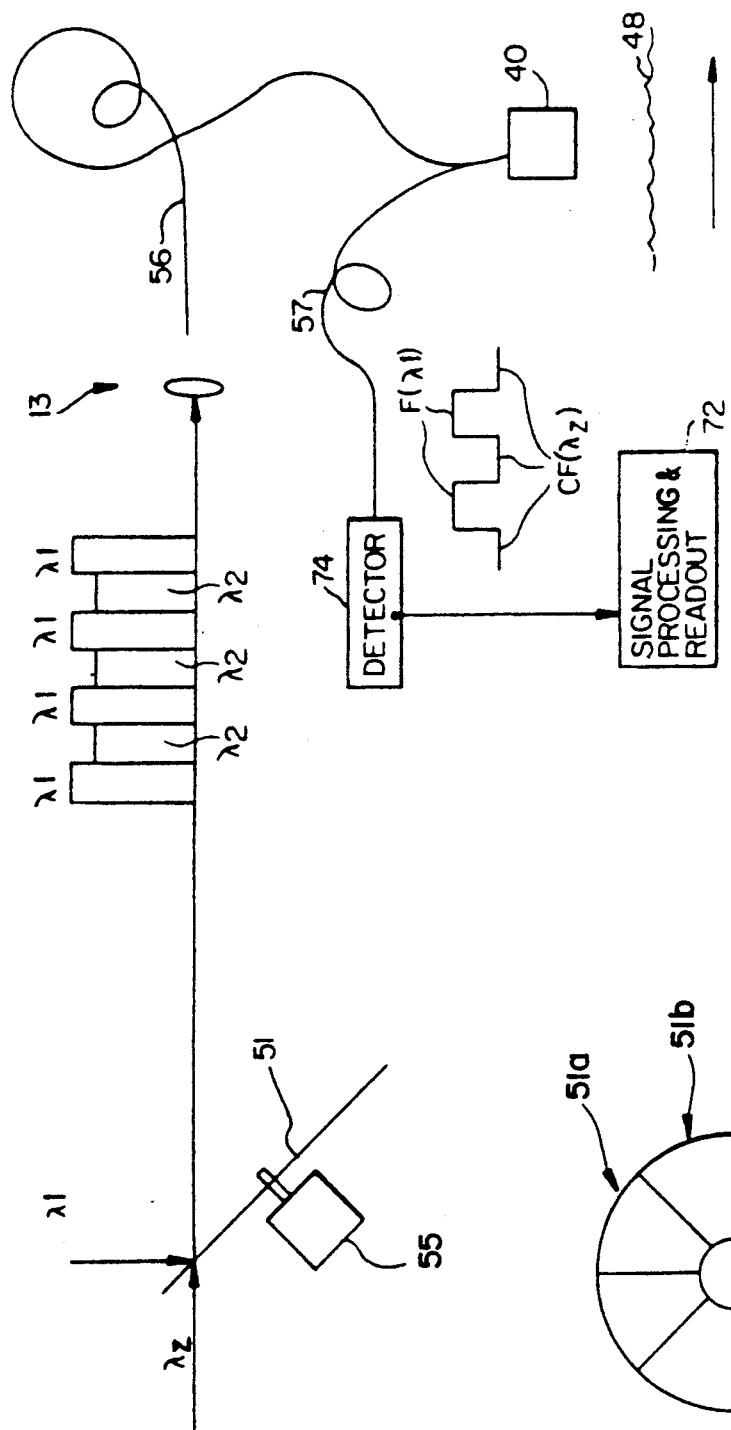
FIG. 6(a) is a schematic diagram of an apparatus used for measuring lignin in a sample with dual excitation wavelength fluorescence spectroscopy.
FIG. 6(b) is a frontal view of chopper wheel (51)

FIG. 6(a) is another embodiment similar to FIG. 5 for measuring the lignin concentration in wood pulp using dual excitation wavelength fluorescence spectroscopy. The same reference numerals are utilized to designate the same or functionally similar parts. Two lasers are operated at two different wavelengths, $\lambda_1$, and $\lambda_2$, for example $\lambda_1 = 337$ nm and $\lambda_2 = 488$ nm. Of course, there is great flexibility in selecting excitation wavelenghts. The two laser beams $\lambda_1$ and $\lambda_2$ are combined by a mirrored chopper wheel (51) rotated by a stepper motor (55). The chopper wheel (51) consists of a series of open slots (51a) alternating with mirrors (51b) as best seen in FIG. 6(b). When the open slot (51a) is at the point of intersection of the two beams, $\lambda_1$ and $\lambda_2$, only $\lambda_2$ passes through and is input through a lens (13) to the source or excitation optical fiber or fiber bundle (56) where it is received and transmitted by probe (40) to a sample (48) such as a pulp mat.

Laser beam $\lambda_1$ passes to the excitation fiber (56) only when the mirror (51b) is at the point of intersection. While laser beam $\lambda_1$ is directed to probe (40) by way of lens (13) and the excitation fiber (56), laser beam $\lambda_2$ is blocked by mirror (51b) of the chopper wheel (51). In this fashion, the laser beam entering the excitation fiber (56) alternates in time between the two excitation wavelengths.

Probe (40) focuses the laser beam on the sample (48) with the sample's emitted fluorescence being collected by the same. Emission or detector fiber or fiber bundle (57) carries fluorescence signals to a detector (74) as previously described with respect to FIGS. 4 and 5. In this embodiment the signal from detector (74) is sent to a system processor arrangement (72) and alternates between that of $\lambda_1$ and $\lambda_2$. During the initial calibration and set-up, a weighting constant, C, may be set to a desired value simply by adjusting the intensity of laser beam $\lambda_2$. The signal from detector (74) will then be a square wave whose amplitude is the desired function, e.g., $F(\lambda_1) - C*F(\lambda_2)$.

The total fluorescent emission from undiluted pulp samples can be expressed as follows:

$$F = Af_1 + Bf_2 \qquad (I)$$

where:
$f_1$ = the fluorescence that correlates well with the concentration of lignin as measured by the standard wet chemical method and expressed as KAPPA Number.
$F_2$ = the fluorescence that does not correlate well with measured lignin concentration.
A and B are constants.

Figure 7A:
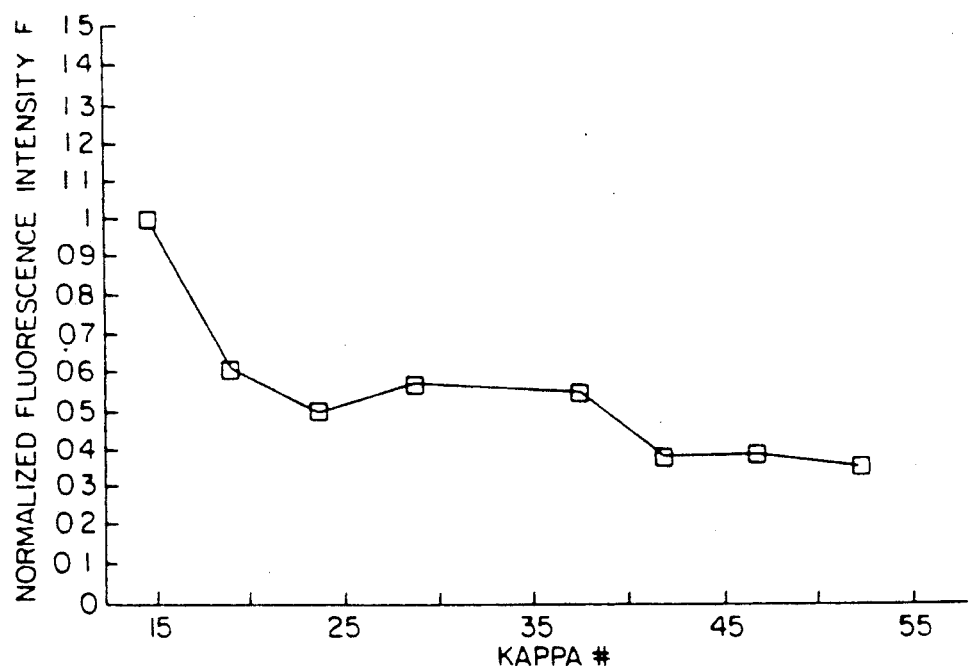
FIG. 7(a) is a plot of fluorescence intensity versus KAPPA Number with excitation at 337 nm.
Figure 7B:
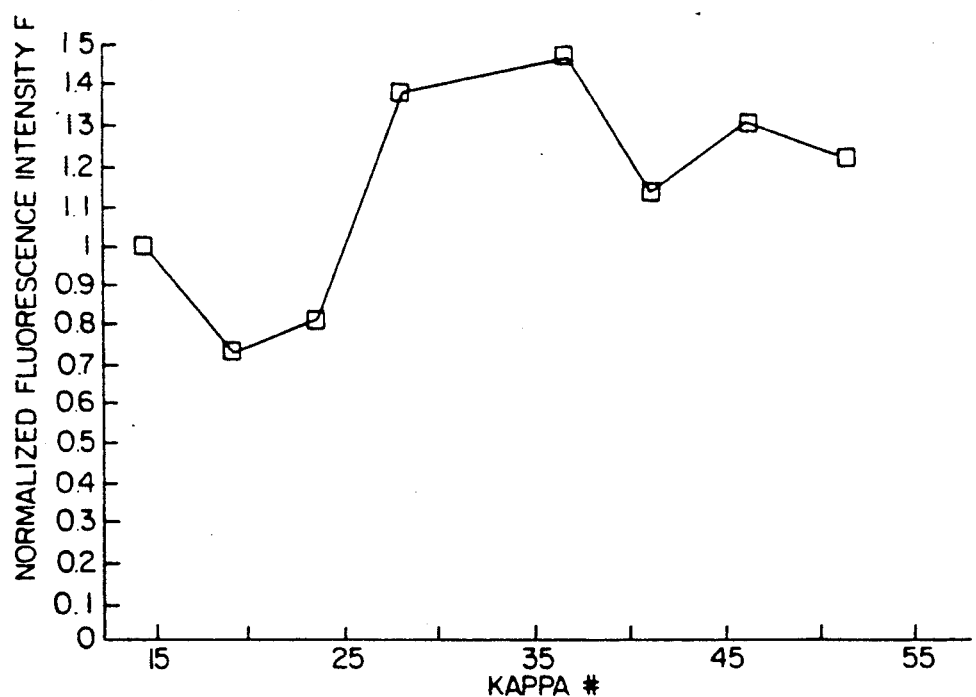
FIG. 7(b) is a plot of fluorescence intensity versus KAPPA Number with excitation at 488 nm.

Because of the $f_2$ component, the correlation between F and Kappa Number is poor, as shown in FIGS. 7(a) and (b), and F cannot be used as a measure of lignin concentration. The data in FIGS. 7(a) and (b) were obtained with a device schematically depicted in FIG. 6(a) set at $\lambda_1 = 337$ nm and $\lambda_2 = 488$ nm. A comparison of FIG. 7(a) with FIG. 7(b) shows that the relative effect of the $f_2$ component is greater when the fluorescence is excited by a longer wavelength source, i.e., 488 nm.

Therefore, equation (I) can be rewritten as follows:

$$F(337) = A(337)*f_1 + B(337)*f_2 \qquad (II)$$

$$F(488) = A(488)*f_1 + B(488)*f_2 \qquad (III)$$

When these two equations (II) and (III) are combined to eliminate the $f_2$ term, the following equation results:

$$\frac{f_1}{D} = F(337) - C*F(488)$$

where:
C and D are constants that are combinations of the original A's and B's.

Figure 8:
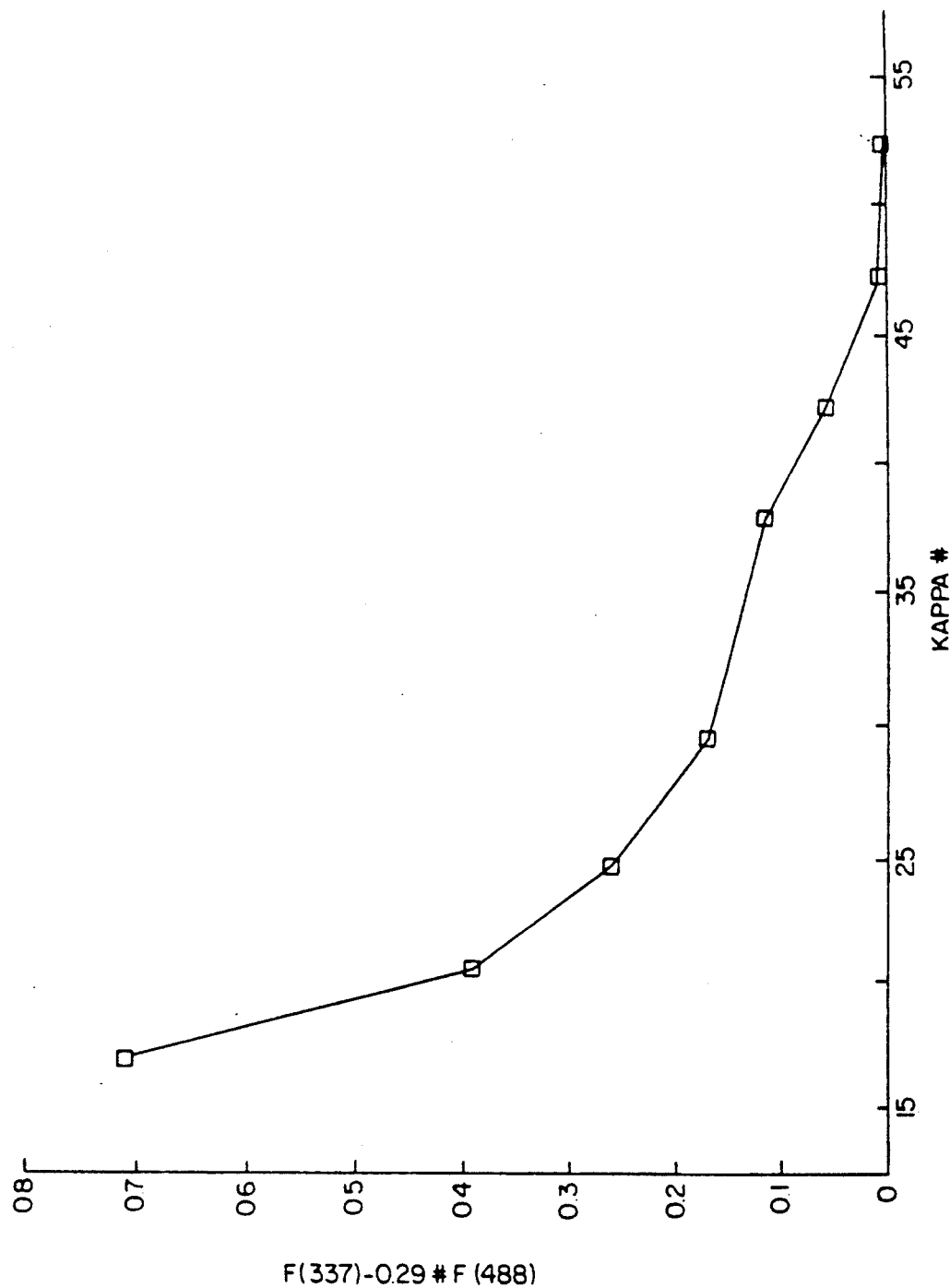
FIG. 8 is plot of response vs. Kappa number combining measured quantities, F (337) and F (488), excitation at 337 nm and 488 nm versus KAPPA Number.

Since $f_1$ provides a good measure of the lignin concentration as expressed by KAPPA Number, the two measured quantities, F(337) and F(488), are used to calculate the relative lignin concentration provided the constant C is known. Empirically, it was determined that the constant C has the value of 0.29 for investigated pulp samples. FIG. 8 shows that combining the measurements in this way gives a well behaved monotonically decreasing function suitable for the determination of KAPPA Number. It remains to be seen if the constant, C, is the same for pulps from different woods and/or different processes. If not, a calibration is simply required to determine this value for a given type of pulp.

Figure 9:
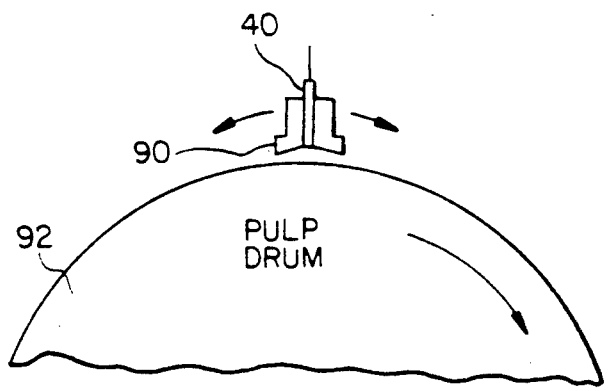
FIG. 9 is a partial schematic view of a device according to the present invention for maintaining a selected distance between a probe used in accordance with the present invention and a pulp drum carrying a layer of pulp.

FIG. 9 shows a mounting for probe (40) in a vacuum sleeve (90) which is engageable at a selected distance from a pulp mat on a pulp drum (92). The signals from probe (40) can be processed in the apparatus of FIGS. 4, 5 and 6(a) to monitor lignin concentration in the pulp mat.

Figure 10:
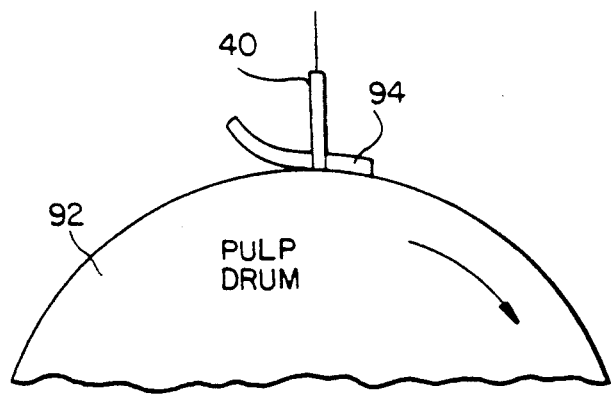
FIG. 10 is a view similar to FIG. 9 of another embodiment of the device.

FIG. 10 shows a contact version of the invention where a probe (40) is in contact with the mat through a standard thickness transparent layer (94) in contact with the mat on the drum (92).

Figure 11:
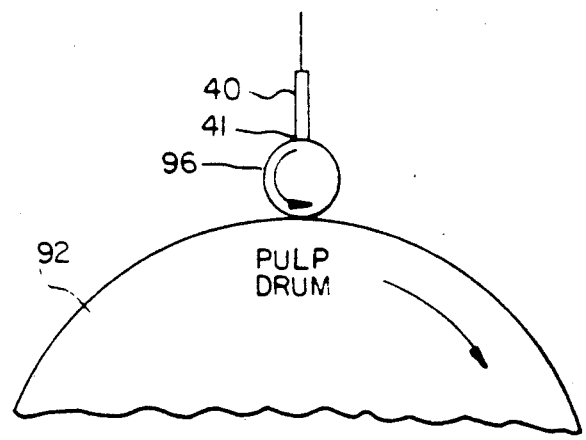
FIG. 11 is a view similar to FIG. 9 of a still further embodiment of the device.

FIG. 11 utilizes probe (40) which is fluid coupled at (41) to the surface of a silica ($SiO_2$) cylinder (96) in contact with the pulp mat on drum (92).

Figure 12:
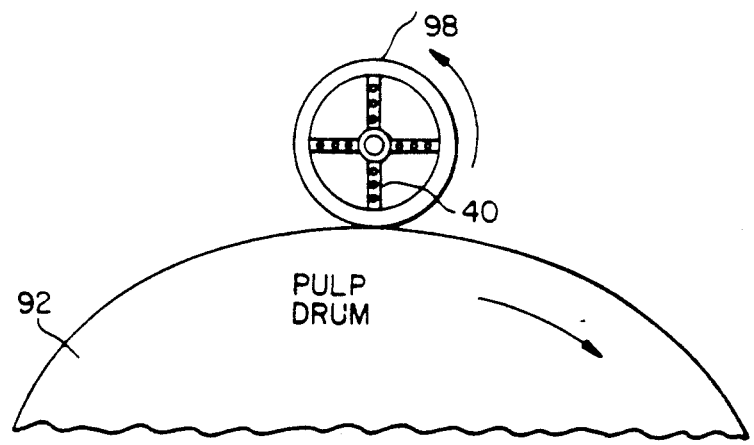
FIG. 12 is a view similar to FIG. 9 of a still further embodiment of the device.

FIG. 12 shows an embodiment where the probe (40) is mounted as a spoke on a quartz cylinder (98) in rolling contact with the mat on drum (92).

Figure 13:
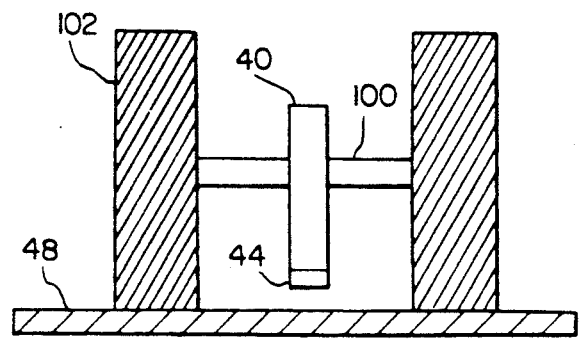
FIG. 13 is a front elevational view of a device for maintaining a selected spacing between a pulp mat and a probe used in accordance with the present invention.

In the embodiment of FIG. 13, the sensing end (44) of probe (40) is held at an accurate and selected distance from pulp mat (48) by mounting the probe (40) on the axle (100) of a pair of rollers (102) rolling against the pulp mat (48).

Figure 14:
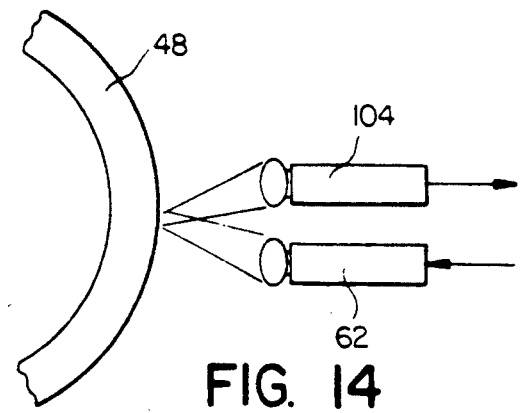
FIG. 14 is a schematic side view of a still further embodiment of the invention for measuring lignin concentration on a pulp mat.

FIG. 14 illustrates a non-contact pulp mat probe arrangement where the pulp mat (48) is illuminated by a light source (62) with fluorescent light being received by light sensor (104), for processing.

Figure 15:
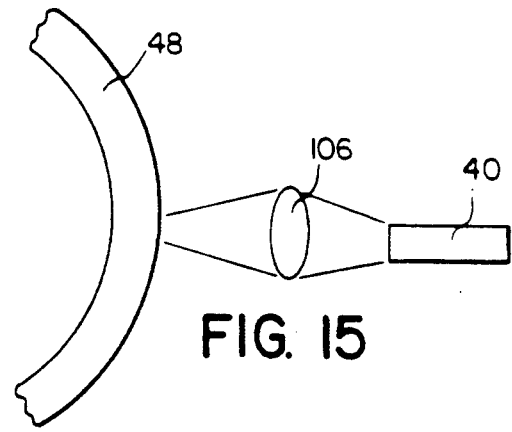
FIG. 15 is a view similar to FIG. 14 showing a further embodiment of the present invention.

In the embodiment of FIG. 15, probe (40) both shines and receives light through a lens (106) to and from the mat (48).

Figure 16:
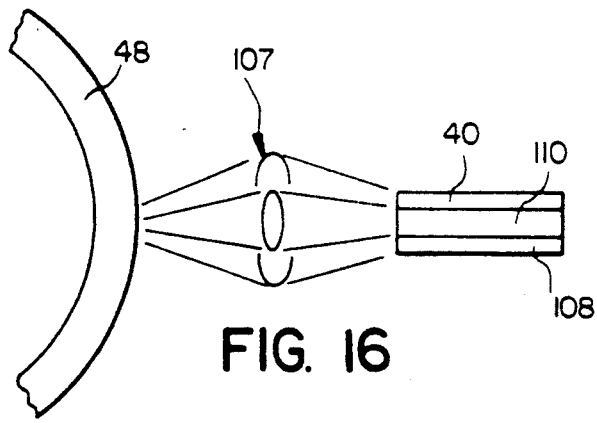
FIG. 16 is a view similar to FIG. 14 showing a still further embodiment of the invention.

In the embodiment of FIG. 16, mat (48) is illuminated by a probe (40) having an outer light source (108) and a central fluorescent response tube (110). A lens (107) having separate inside and outside elements for shining and receiving the light is provided between the probe and the pulp mat.

Figure 17:
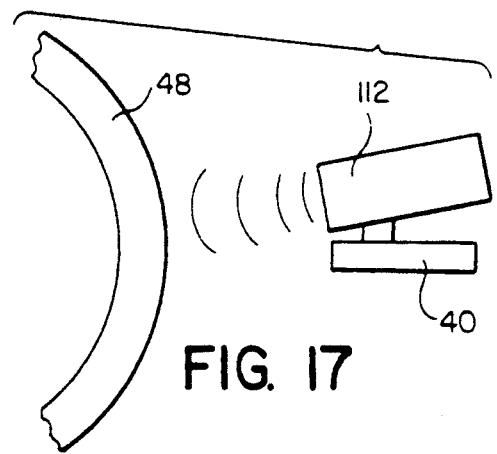
FIG. 17 is a view similar to FIG. 14 of a still further embodiment of the invention.

In the embodiment of FIG. 17, probe (40) is set at a known desired distance from mat (48) by a proximity sensor (112) such as an ultrasonic distance instrument which is physically connected to the probe. In the non-contact version of the present invention, maintaining a set and accurately known distance between the probe face and the mat is essential to avoid variations in light intensity which, rather than due to lignin concentration, is due to distance variations.

Embodiments of the invention for measuring lignin concentration in black liquor or pulp slurries are shown in FIGS. 18–21.

Figure 18:
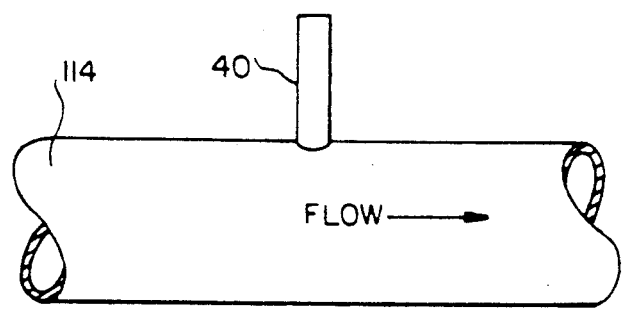
FIG. 18 is a side elevational view of a probe and flow tube combination for measuring the lignin concentration in pulp slurry or in black liquor according to the present invention.

FIG. 18 shows probe (40) which may be the same design as the probes utilized in the equipment of FIGS. 4, 5 and 6(a) engaged to an aperture in a flow tube (114) which contains a flow of black liquor or pulp slurry.

Figure 19:
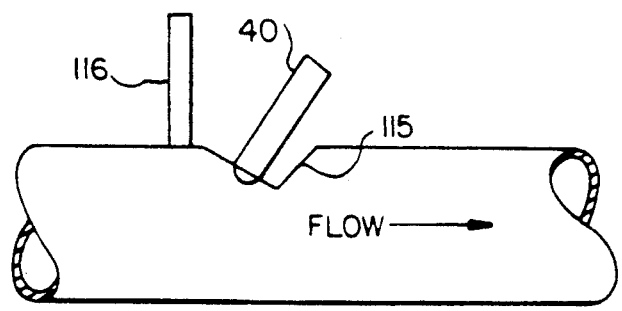
FIG. 19 is a view similar to FIG. 17 of a different embodiment thereof.

In the embodiment of FIG. 19, probe (40) penetrates tube (114) in a recess (115). The sensor face of probe (40) is serviced by a fluid injector (116) which may be used to scour and clean the sensor face.

Figure 20:
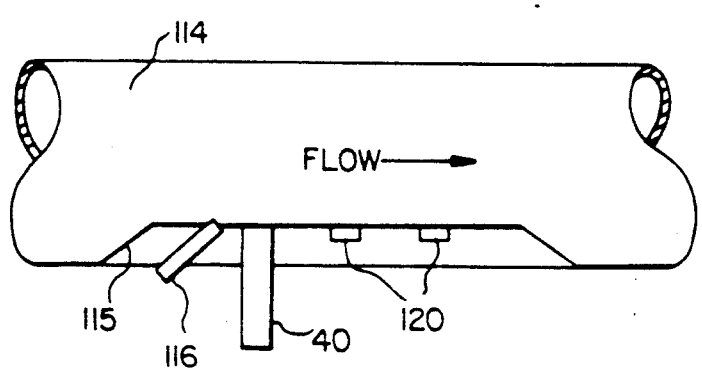
FIG. 20 is a view similar to FIG. 17 of a still further embodiment thereof.

A similar injector (116) is used in a recess (115) of the tube (114) in the embodiment of FIG. 20 where probe (40) is mounted next to multiple windows (120) which are used to insure the presence of black liquor flow. A single long window may replace the two windows (120).

Figure 21:
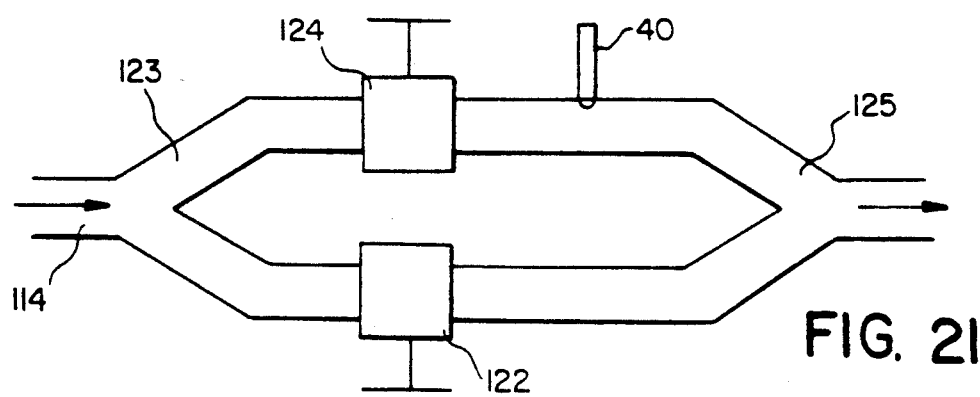
FIG. 21 is a view similar to FIG. 18 of a further embodiment of the present invention.

FIG. 21 shows an embodiment of the invention where flow is normally conducted through a supply valve (122) downstream of a Y-connection (123) in the flow pipe (114). When a real-time measurement is to be taken, valve (122) is closed and a second valve (124) is opened which causes the stream to pass probe (40). The streams are reconnected at a second Y-connection (125).

Figure 22:
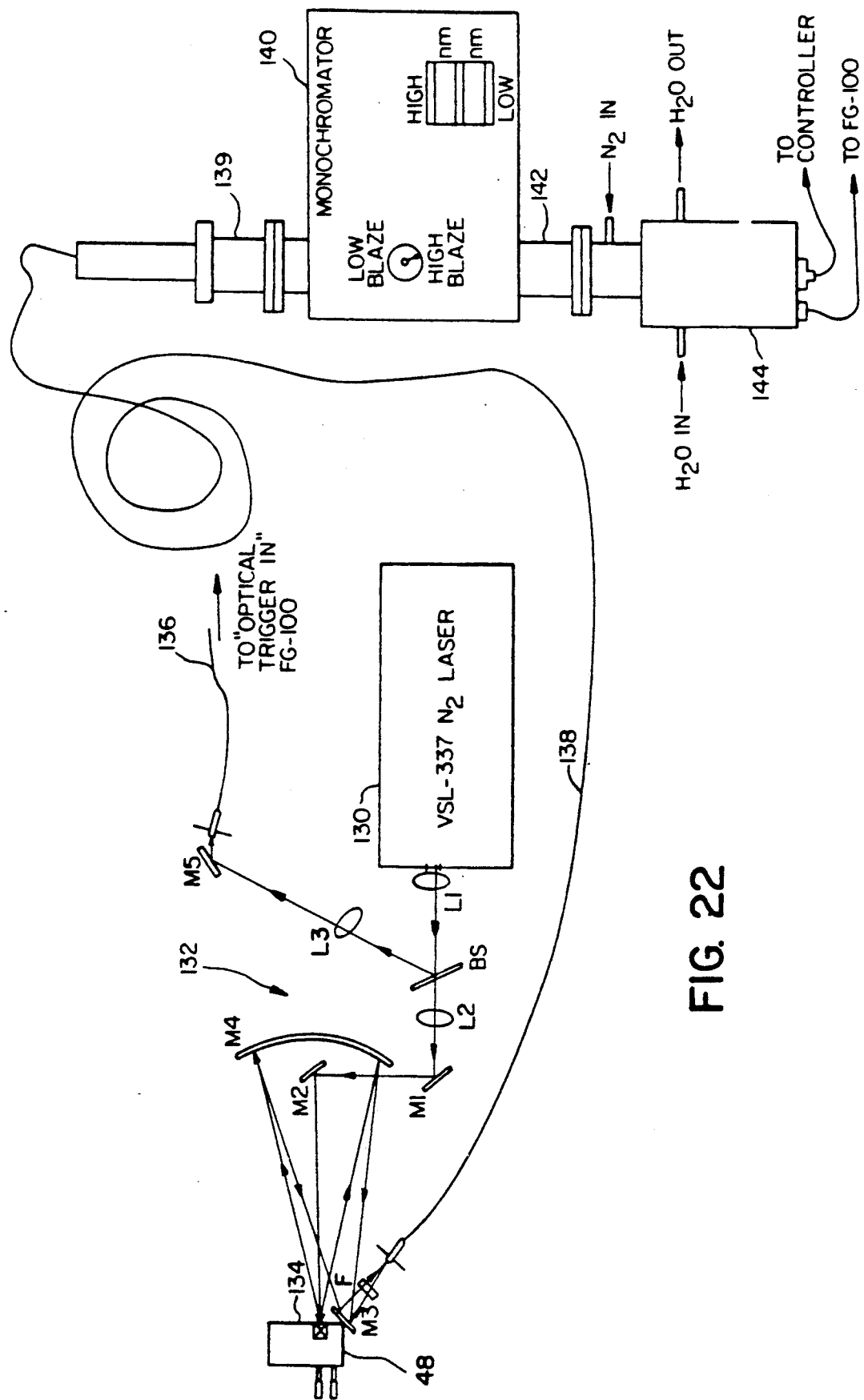
FIG. 22 is a schematic block diagram of a laboratory set up for verifying the excitation wavelengths and time resolved fluorescence techniques of the present invention.

FIG. 22 illustrates an apparatus for verifying the usefulness of the invention which comprises a nitrogen laser (130) which supplies light to an optical arrangement of lenses and mirrors (132), to a sample 48 mounted on a translator (134) and to a fiber (136) which supplies a reference light signal as a trigger to electronic sensing equipment. Fluorescent light is supplied over a fiber bundle (138) to the input (139) of a monochromator (140). The output (142) of monochromator (140) is supplied to a detector (144) such as an IRY-690G/B/Par detector for example.

Figure 23:
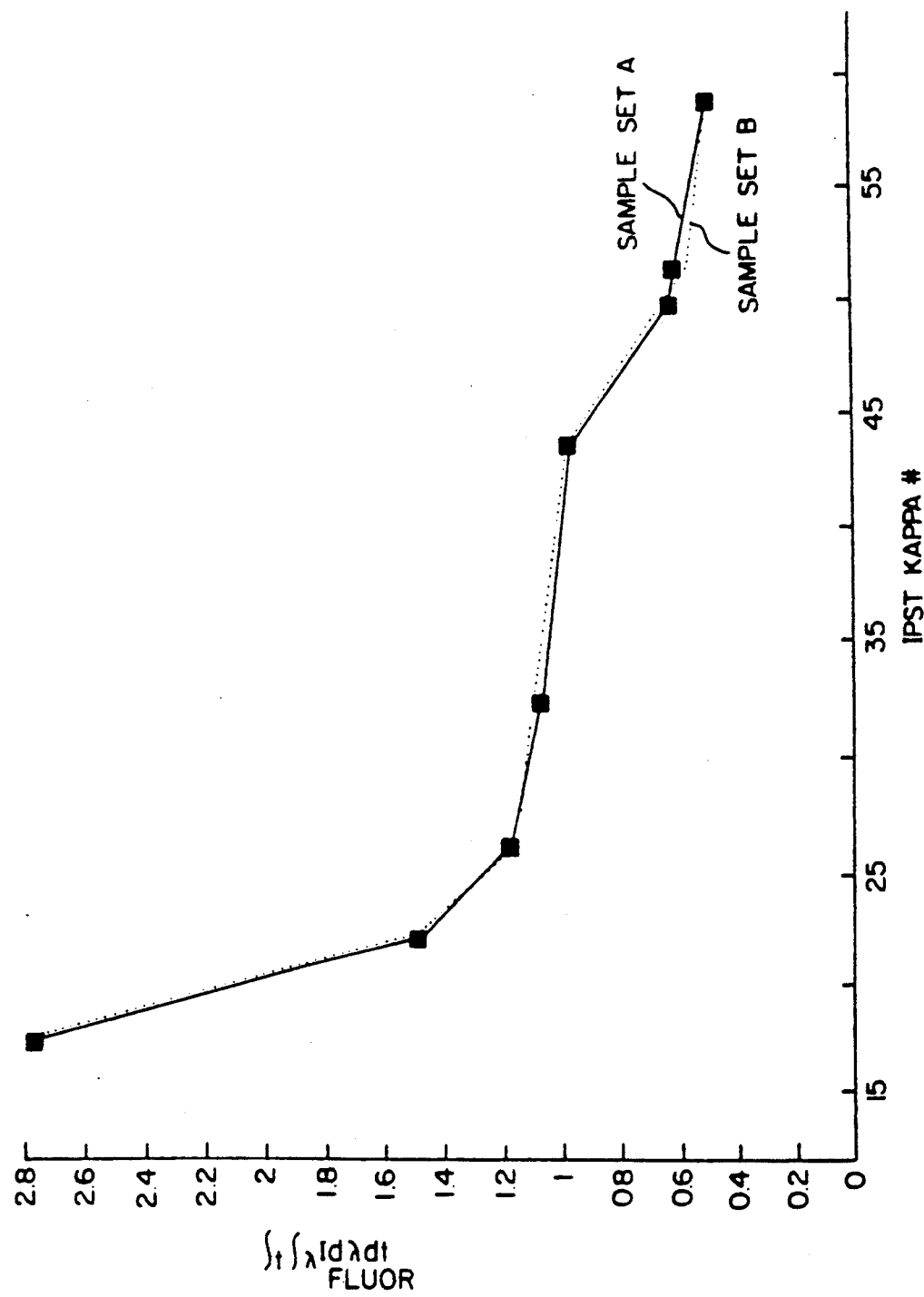
FIG. 23 is a plot of fluorescence intensity vs. KAPPA Number using time resolved fluorescence at 12 ns delay using the device of FIG. 22.

The apparatus of FIG. 22 was utilized to measure fluorescence at time delays of 00, 04, 06, 08, 10 and 12 nanoseconds (ns) to reveal the correlation between fluorescent light intensity and KAPPA Number. FIG. 23 is a plot of fluorescent intensity versus KAPPA Number using time resolved fluorescence at 12 ns delay with the device shown in FIG. 22. The time delay ($T_0$) equals 12 ns to a final time ($T_1$) of 2,000 ns with wavelength integration of 360 to 700 nm and excitation at 337 nm.

While the specific embodiments of the invention have been shown and described in detail to illustrate the application of the principles of the invention, it will be understood that the invention may be embodied otherwise without departing from such principles.

What is claimed is:

1. An apparatus for measuring lignin concentration with time resolved fluorescence in an undiluted wood pulp or black liquor sample, on a real-time, in situ basis, comprising:

light source means for applying excitation light pulses at a selected wavelength and at known time intervals to the undiluted sample for causing the lignin concentration to produce fluorescent emission light with a fluorescence intensity that monotonically decreases in a quenched fluorescence regime;

light detector means for measuring the emission light at the known time intervals and establishing signals indicative thereof;

switching means for turning said light detector means on at precise specified time intervals after each excitation light pulse; and signal processing means connected to the light source means and the light detector means for comparing intensities of the emission light from the lignin in the quenched fluorescence regime to the intensities of the excitation light pulses on a time resolved basis for providing a measurement of the lignin concentration in the undiluted sample as a function of the time resolved emission light intensity.

2. An apparatus according to claim 1, including a probe having a sensing end for facing the sample, said probe being connected to the light source means for conveying the excitation light pulses to the sample, said probe being connected to said light detector means for conveying emission light from the sample.

3. An apparatus according to claim 2, including means for mounting the probe at a selected distance from the sample.

4. An apparats for measuring lignin concentration with phase resolved fluorescence in an undiluted wood pulp or black liquor sample on a real-time, in situ basis, comprising:

light source means for applying continuous excitation light at a selected wavelength to the undiluted sample for causing the lignin concentration to produce fluorescent emission light with a fluorescence intensity that monotonically decreases in a quenched fluorescence regime;

means for modulating the continuously applied excitation light;

light detector means for measuring the modulated emission light of the lignin in the quenched fluorescence regime and establishing signals indicative thereof;

a reference light provided to the light detector means modulated in accordance with the modulated applied excitation light; and signal processing means connected tot he light detector means for correlating intensity with respect to phase of the modulated emission light to the intensity of the modulated excitation light for providing a measurement of the lignin concentration in the undiluted sample on a real-time, in situ basis as a function of the phase resolved emission light intensity.

5. An apparatus according to claim 4, including a probe having a sensing end for facing the sample, said probe being connected to the light source means for conveying the modulated excitation light to the sample and said probe being connected to said light detector means for conveying modulated emission light form the sample.

6. An apparatus according to claim 5, including means for mounting the probe at a selected distance from the sample.

7. An apparatus for measuring lignin concentration in an undiluted sample on a real-time, in situ basis, comprising:

first and second light sources for supplying excitation lights at first and second selected and different wavelenghts to the undiluted sample for causing the lignin concentration to provide fluorescent emission light with a fluorescence intensity;

means for selectively alternating transmission of the first and second wavelenghts of excitation light to the undiluted sample;

light detector means for measuring the emission light of the lignin on the quenched side for both wavelengths and establishing first and second signals indicative thereof;

signal processing means connected to the light detector means for measuring the signals of the emission light at both wavelengths and comparing and signals to the intensity of the excitation light for both wavelengths; and means for converting the compared signals into a function that monotonically decreases in a quenched fluorescence regime to provide a measurement of the lignin concentration in the sample that uses the emission light intensity for both wavelengths.

8. An apparatus according to claim 7, including a probe having a sensing end for facing the sample, said probe being connected to the first and second light sources for conveying the excitation light at both wavelenghts to the sample, said probe being connected to said light detector means of conveying emission light from the sample.

9. An apparatus according to claim 8, including means for mounting the probe at a selected distance from the sample.

10. An apparatus according to claim 7, wherein said fist and second light sources include two lasers.

* * * * *